US006220751B1

United States Patent
DiGiacomo et al.

(10) Patent No.: US 6,220,751 B1
(45) Date of Patent: Apr. 24, 2001

(54) APPARATUS FOR ENHANCING CEPHALOMETRIC IMAGES

(75) Inventors: Ellen V. DiGiacomo; Rita J. Johnson, both of Concord, MA (US)

(73) Assignee: Millennium Advantage Products, LLC, Concord, MA (US)

( * ) Notice: Subject to any disclaimer, the term of this patent is extended or adjusted under 35 U.S.C. 154(b) by 0 days.

(21) Appl. No.: 09/211,247

(22) Filed: Dec. 14, 1998

(51) Int. Cl.[7] .................................................. A61B 6/14
(52) U.S. Cl. ............................................. 378/182; 378/185
(58) Field of Search ............................ 378/38, 156, 158, 378/159, 168, 169, 174, 182, 185

(56) References Cited

U.S. PATENT DOCUMENTS

| | | | |
|---|---|---|---|
| 2,247,451 | * 7/1941 | Rawls | 378/169 |
| 4,082,957 | 4/1978 | Morlan | 250/482 |
| 4,561,054 | * 12/1985 | Andrews et al. | 378/174 |
| 5,058,147 | 10/1991 | Nishikawa et al. | 378/38 |
| 5,376,801 | * 12/1994 | Saotome et al. | 378/185 |
| 5,454,023 | 9/1995 | Asikainen | 378/156 |
| 5,574,768 | * 11/1996 | McLean | 378/185 |
| 5,734,693 | 3/1998 | Quint et al. | 378/185 |

OTHER PUBLICATIONS

Dentsply Gendex Orthoralix 9000, Technical Specification Sheet.
DenOptix Gendex Digital Imaging System, Technical Specification Sheet.
Dentsply Gendex Orthoralix S/SD2, Technical Specification Sheet.
Planmeca PM 2002 CC Proline Technical, Specification Sheet.
America Dental, Dental Imaging Accessories Catalog.
Hollico Products, Inc., Cepth–Traxx, Technical Specification Sheet.

* cited by examiner

Primary Examiner—Robert H. Kim
Assistant Examiner—Drew A. Dunn
(74) Attorney, Agent, or Firm—George A. Herbster; Pearson & Pearson

(57) ABSTRACT

A filter for use in an x-ray film cassette for cephalometric imaging. The filter is interposed between the x-ray film being exposed an adjacent x-ray conversion screen. The filter has a substantially optically opaque portion that is aligned with the patient's forehead and chin and a transparent portion. An image produced on the film depicts skeletal features in the area aligned with the transparent portion and both skeletal and soft tissue features in an area aligned with the substantially optically opaque portion.

22 Claims, 4 Drawing Sheets

APPARATUS FOR ENHANCING
CEPHALOMETRIC IMAGES

BACKGROUND OF THE INVENTION

1. Field of the Invention

This invention generally relates to x-ray imaging and more specifically to apparatus for enhancing a cephalometric image in a dental x-ray.

2. Description of Related Art

In dentistry and other medical disciplines diagnoses and treatments can be aided by x-ray imaging of the skull. This invention is particularly directed to cephalometric imaging for obtaining a lateral view of the skull by means of transmissive radiographic imaging directed transversely across the median plane. Generally speaking, such an image is obtained by positioning a patient's head between an x-ray source and a film cassette. The x-ray energy is then directed toward the patient's head to the cassette to produce a full image of the skull on the film.

However, given the wide range of densities of the skeletal and soft tissue portions of the head, a conventional x-ray will either properly expose the skeletal portions of the head and over-expose the soft tissue portions or properly expose the soft tissue portions and underexpose the skeletal portions. As known, this result occurs because the areas of different density in the head will attenuate the x-ray energy differently. Normally a technician will adjust the exposure to expose the skeletal portions properly. Consequently, the resulting image will be either devoid of any soft tissue information or have only minimal information that will not be easily discerned by a visual inspection of a film image.

A number of approaches have been taken in an attempt to overcome this problem so that a single x-ray exposure will provide good image detail of both skeletal and soft tissue areas of a patient's head. One approach involves interposing a wedge-shaped shield for attenuating the intensity of the x-ray passing through an area dominated by soft tissue. In some cases these shields, or "soft tissue shields," are shaped metal devices that attach to the exterior of the film cassette. For cephalometric imaging, the soft tissue shield mounts to extend vertically across the front end of the cassette, that is, the end of the cassette aligned with the frontal area of the patient's head including the forehead and chin areas.

U.S. Pat. No. 5,454,023 (1995) to Asikainen depicts a cephalostat with a soft tissue shield, or filter, that is interposed between the x-ray source and the patient. This cephalostat uses the filter to attenuate the intensity of the x-rays before they reach the soft tissue areas of the patient.

U.S. Pat. No. 5,058,147 (1991) to Nishikawa et al. depicts another embodiment of dental x-ray apparatus for providing panoramic or cephalometric images. This apparatus includes a first cassette holder for a cephalometric cassette and a second cassette holder for a panoramic cassette. A control mechanism moves an x-ray generator between two positions depending upon the type of image that has been selected. In addition, the control system alters radiation slits on the x-ray generator to alter the characteristic x-ray energy emitted from the generator for the two different image types.

Still another approach utilizes specially constructed film cassettes. Normal film cassettes provide an image on x-ray film by placing the film having one emulsion side against one conversion screen or having two emulsion sides between two conversion screens. The conversion screens convert impinging x-radiation into energy having a wavelength that corresponds to a sensitive film wavelength. For example, if the film is sensitive to blue light, the conversion screen will be formed to produce blue light in response to x-ray radiation with the intensity of the light being a function of the x-ray intensity.

Generally a conversion screen has a uniform response characteristic. That is, if the screen is subjected to a uniform radiation intensity, it will produce an even exposure on the film adjacent to it. Specially constructed conversion screens alter the response characteristic over different areas of the screen. In one such system, the conversion of areas that will image predominantly skeletal portions convert a greater portion of the x-ray radiation to light than the areas that will image predominantly soft tissue. Consequently, the soft tissue areas will be exposed less than the skeletal areas.

U.S. Pat. No. 5,734,693 (1998) to Quint et al. depicts a radiation exposure system that incorporates such specially constructed conversion screens and optical filters in a film cassette. X-ray radiation received from the patient passes through a front face of the cassette, a first conversion screen, an optical filter, the x-ray film and a second screen. The filter has an area of a first optical density of a first material and a second area of a second optical density. In the specific embodiment, the second area is formed by removing corresponding portions of the first material. This patent also suggests using an optical filter formed of a partially radiation opaque, absorbing or blocking material thereby to control the exposure of the second screen. In this apparatus, at least one of the screen layers includes an area of different amounts or reactant material, a selective grading from a front end of the screen to the back end being described.

In still another approach, the x-rays from the patient energize a photoarray connected to a computer system for scanning an x-ray image. With such an image it is possible to enhance portions of the image so that soft tissue appears in the final image.

Each of the foregoing approaches have certain drawbacks. Specially designed equipment, such as described n the Asikainen and Nishikawa et al. patents, is much more expensive than conventional dental x-ray machines. The nature of many dental practices can not justify the expense of obtaining such special equipment. Such practices have sought and do seek to obtain good cephalometric imaging by the use of special cassettes. However, such special cassettes are also expensive and are limited in application. This requires a larger inventory of film cassettes and the development of procedures for assuring that, for a given x-ray, the proper cassette is selected.

SUMMARY

Therefore, it is an object of this invention to provide a simple apparatus for enhancing x-ray images of skeletal and soft tissue areas.

Another object of this invention is to provide a simple apparatus for enhancing cephalometric x-ray images of skeletal portions of the skull and the soft tissues at the front of the head.

Yet another object of this invention is to provide a simple apparatus for enhancing x-ray images of skeletal and soft tissue areas that is easy to use.

Still yet another object of this invention is to provide a simple apparatus for enhancing x-ray images of skeletal and soft tissue areas that is inexpensive to produce.

Still another object of this invention is to provide a simple apparatus that can be inserted in or removed from a standard x-ray film cassette to provide cephalometric or conventional images respectively.

In accordance with one aspect of this invention an apparatus in the form of a filter enhances a cephalometric image on a film produced by directing an x-ray beam from a source through a patient's head to a cassette containing the film in a plane parallel to the median plane. The cassette has first and second ends and a uniformly responsive conversion screen for responding to x-rays impinging on the screen by producing energy that exposes the film. The filter comprises a sheet interposed between the film and the screen that has a substantially optically opaque portion that is aligned with the patient's forehead and chin. The filter also has a substantially transparent portion. An image produced on the film depicts skeletal features in the area aligned with said transparent portion and skeletal and soft tissue features in the area aligned with the substantially optically opaque area.

In accordance with another aspect of this invention, a filter enhances a cephalometric image on a film produced by directing an x-ray beam from a source through a patient's head to a cassette containing the film that is pre-positioned in a plane parallel to the median plane to receive x-rays traversing the patient's head, the cassette terminating in a forward end proximate the patient's forehead, nose and chin and a rearward end proximate the back of the patient's head. The cassette has first and second uniformly responsive conversion screens for responding to x-rays impinging on the screens by producing energy that exposes the film between the first and second screens. The filter includes a sheet interposed between the film and one of the screens. The sheet has a substantially optically opaque portion extending perpendicularly to the axis across the film so that the opaque portion is aligned with the patient's forehead and chin. A substantially transparent portion of the filter extends from the rearward end forward toward the opaque portion. An image produced on the film depicts skeletal features in the area aligned with said transparent portion and skeletal and soft tissue features in the area aligned with the substantially optically opaque area.

In accordance with still another aspect of this invention a cassette for use in obtaining cephalometric images on an x-ray film includes a frame elongated along a cassette axis that carries first and second parallel conversion screens having a substantially uniform sensitivity to impinging x-rays across the area thereof. The cassette, in use, positions the first conversion screen intermediate an x-ray source and the second conversion screen. A film holder positions the film between said first and second conversion screens whereby energy from the first and second conversion means is directed toward film in said holding means. A sheet filter formed of an exposed film sheet is interposed between the film holder and the second screen. This sheet filter has a substantially optically opaque portion extending across the exposed film sheet transversely to the cassette axis for alignment with the forehead, nose and chin of a patient. The filter additionally includes a substantially transparent portion whereby an image produced on the film depicts skeletal features in the area aligned with said transparent portion and skeletal and soft tissue features in the area aligned with the substantially optically opaque area.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

DESCRIPTION OF ILLUSTRATIVE EMBODIMENTS

Figure 1:
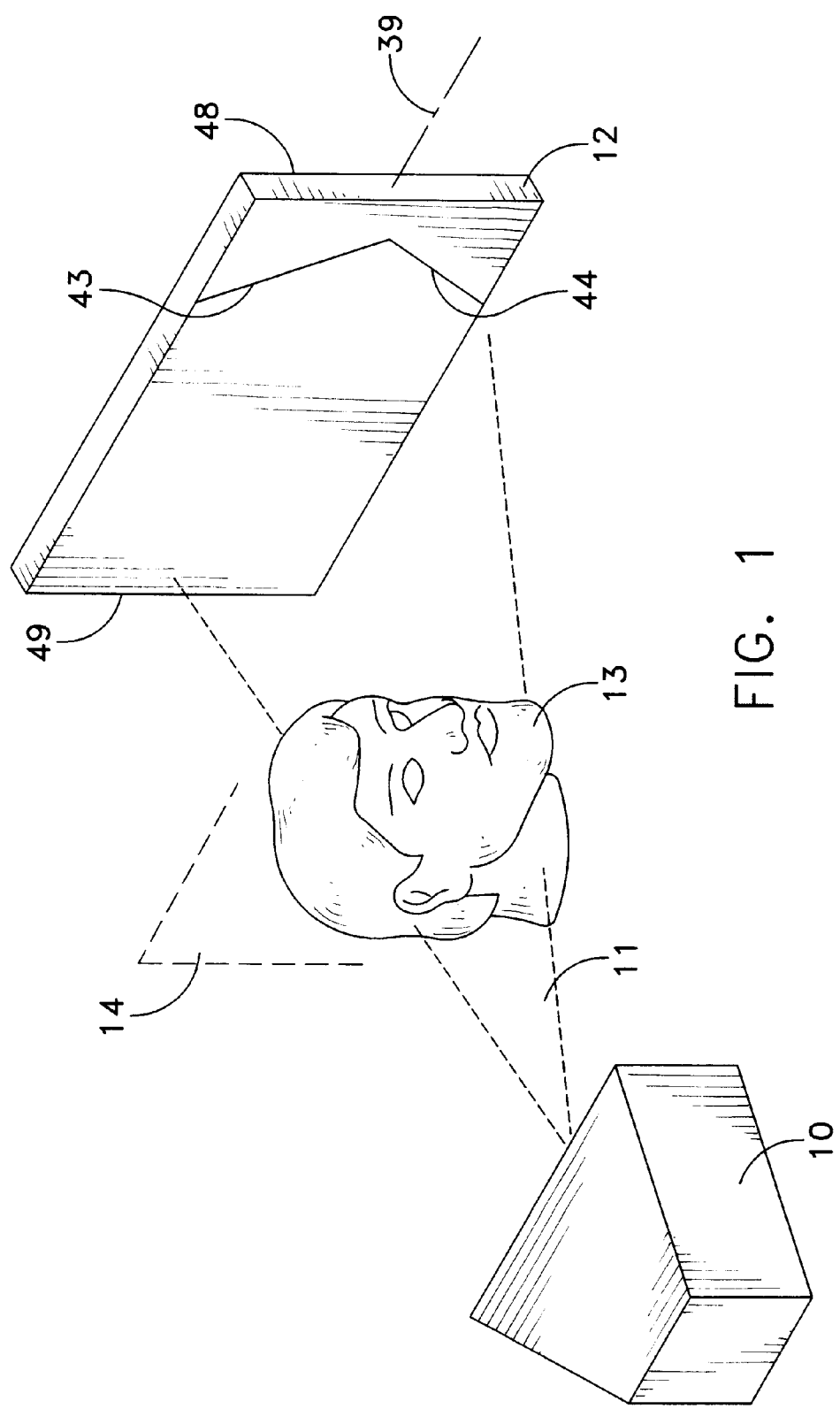
FIG. 1 is a perspective view depicting an x-ray source, patient and film cassette in an orientation for providing a cephalometric image of the patient.

FIG. 1 depicts, for reference purposes, a typical set up for producing a cephalometric image. The apparatus includes a conventional x-ray source 10 typically in the 80 to 90 kv range that directs x-rays 11 toward a cassette 12. The operator positions a patient's head 13 in alignment between the x-ray source 10 and the cassette 12 such that the cassette 12 and the median plane 14 through the patient are substantially parallel. When an operator energizes the x-ray source 10, x-ray radiation directed through the patient's head 13 onto the cassette 12 exposes an x-ray film in the cassette 12 and thereby produces an image as a sagittal view.

As known, x-rays attenuate differently depending upon the density of the path between the x-ray source 10 and the cassette 12. At higher densities, such as those encountered in skeletal elements, attenuation is at a maximum value. The attenuation in soft tissue is significantly less. Consequently, if one adjusts for an optimal exposure for the skeletal elements through maximum density, film portions aligned with soft tissue will be over exposed with a consequent loss of any physiological detail in the resulting image.

Figure 2:
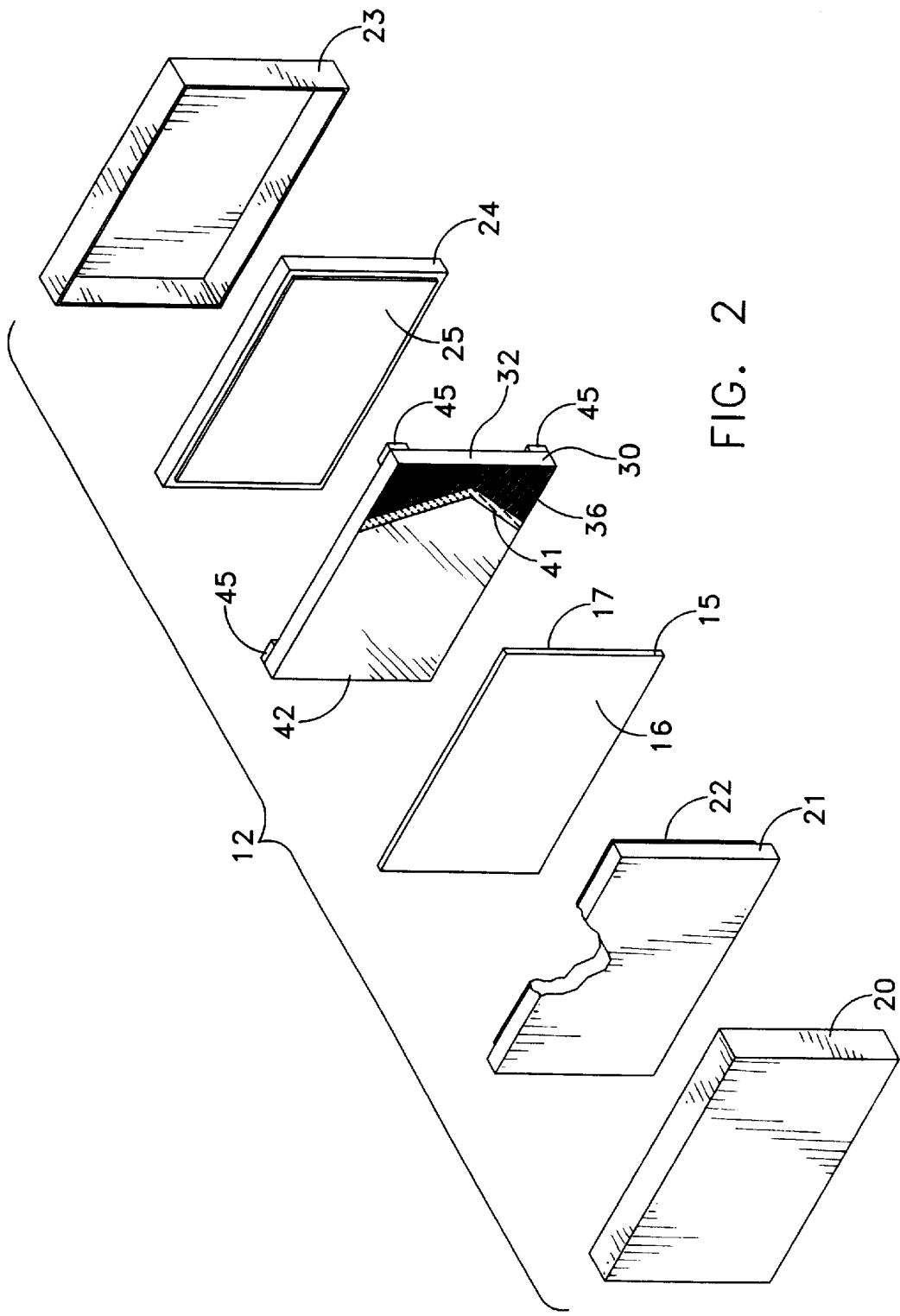
FIG. 2 is an exploded view of one embodiment of a film cassette an optical filter in accordance with this invention.
Figure 3:
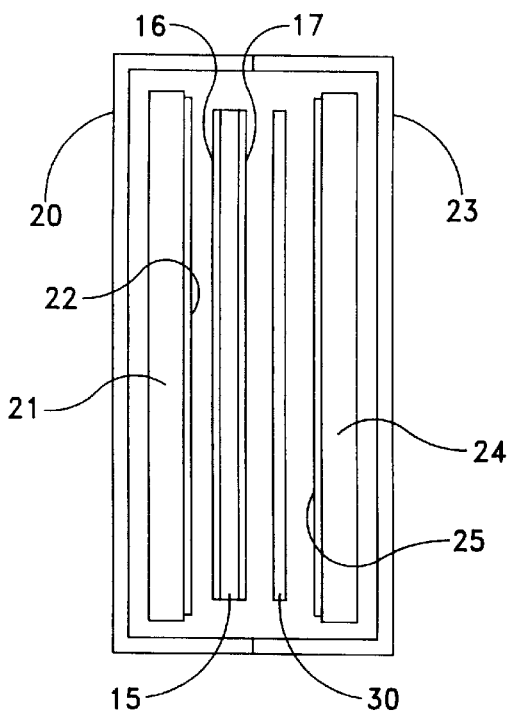
FIG. 3 is a view of the cassette in FIG. 2 in an assembled form.

FIGS. 2 and 3 depict one embodiment of a film cassette 12 modified in accordance with this invention. Using the term "front" to indicate a direction toward the x-ray source 10 in FIG. 1, the cassette 12 carries an x-ray film in a holder, not shown, as a sheet 15 having a front emulsion surface 16 and a rear emulsion surface 17. Such films are typically called double emulsion films. The cassette 12 comprises a first or front frame 20 that carries a first or front conversion screen 21. The conversion screen 21 has a reactant surface 22 juxtaposed the emulsion surface 16 of the film. The reactant surface 22 has a uniform response across the entire area of the screen.

The cassette 12 additionally includes a second or rear frame 23 and a second or rear conversion screen 24 with a reactant surface 25 that provides a substantially uniform response. The reactant surface 25 faces the emulsion surface 17 on the film 15.

As is known, the dominant contributors to the image produced on a film 15 are light from the reactant surface 22 transferred to the emulsion surface 16 and light from the reactant surface 25 that interacts with the emulsion surface 17. To a lesser degree film exposure is dependent upon direct action of the x-rays on the film as well as light from the reactant surface 22 that interacts with the emulsion 17 and conversely light from the reactant surface 25 that interacts with the emulsion 16.

In accordance with this invention, the cassette 12 additionally includes apparatus in the form of a filter 30 that is interposed between the reactant surface 25 and the emulsion 17. Alternatively, a filter, such as filter 30, can be interposed between the reactant surface 22 and the emulsion 16.

Figure 4:
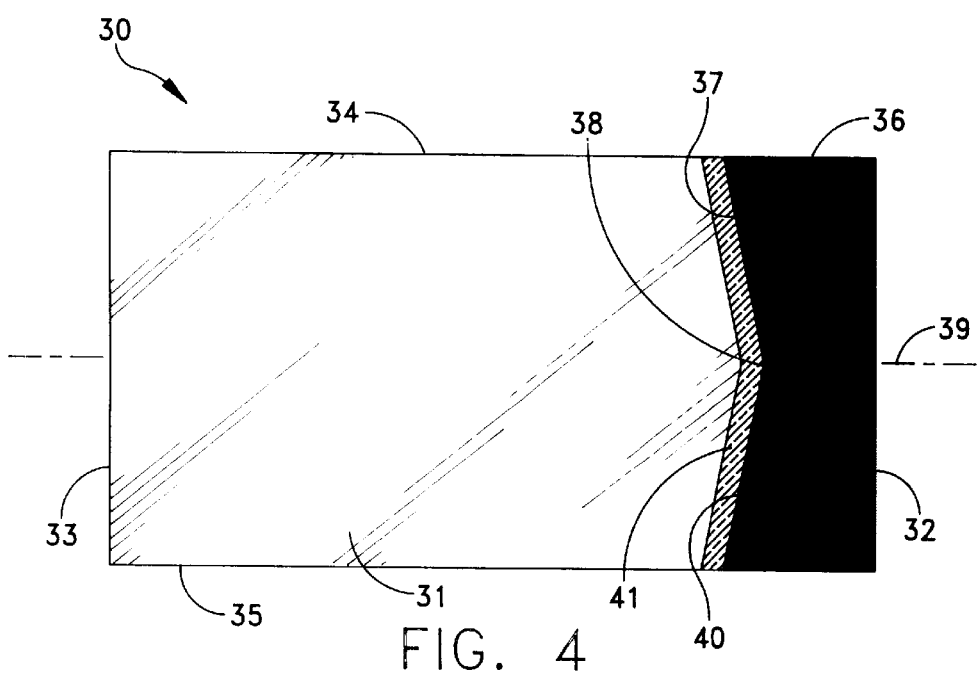
FIG. 4 is a plan view of the optical filter shown in FIGS. 2 and 3.

FIG. 4 depicts the organization of the filter 30 in greater detail. In a preferred embodiment the filter 30 comprises a sheet of film 31 with a positive image. For purposes of explanation, the film 30 has a forward edge 32, a rearward edge 33, a top edge 34 and a bottom edge 35. At the forward edge 32 the film 31 includes a substantially opaque portion 36. By "substantially opaque", it is meant that the exposure of the portion 36 produces a filter that attenuates substantially all the energy that would otherwise transfer from the reactant surface 25 to the emulsion 17 as shown in FIGS. 2 and 3. This opaque portion extends from the forward edge 32 toward the rearward edge 33. It terminates at an oblique upper boundary 37 that extends from the edge 34 to an apex 38 on a central horizontal axis 39. An oblique lower boundary 40 mirrors the boundary 37 and extends from the bottom edge 35 to the apex 38. 2.

In a preferred embodiment the film is formed with an optional band 41 of constant width that extends rearwardly from the boundaries 37 and 40. This area is preferably formed as a semi-opaque or semi-transparent area or band that might attenuate any transfer of energy from the reactant screen 25 to the emulsion 17 by a factor of 50% to 90%.

FIG. 1 depicts the cassette 12 as extending along the axis 39 and defining forward end 48 transverse to the axis 39 and a parallel rearward end 49. As will be apparent from FIGS. 1 and 2, the forward edge 32 and opaque portion 36 of FIG. 2 will be disposed proximate the end 48.

As a specific example, good results have been obtained with a filter 30 comprising an 8"×10" film with a black portion 36 providing about 100% attenuation and a grey portion 41 providing about 80% attenuation. The apex 38 is located about 1⅝" rearward of the forward edge 32. The portion 36 widens to about 2¼" at the top edge 34 and the bottom edge 35. The band 41 has a width perpendicular to the boundaries 37 and 40 of about ½". The balance of the sheet 31, the portion 42, is transparent.

A positive film image as shown in FIG. 4 is readily obtained through conventional means. It has been found, for example, that conventional graphics software can produce an image having any desired shape and range of opacities. Once shapes and opacities are determined, it is merely necessary to generate a negative of that image. Thereafter the actual filters are produced merely by printing the image on a film to produce the positive image that forms the filter 30.

In use a technician first inserts the optical filter 30 into the cassette 12. Adhesive tabs 45 mounted at the corners of the optical filter 30 can facilitate the attachment of the optical filter against the screen 24 thus to maintain it in place when the film is inserted into the cassette. Alternatively the technician can attach the filter to the screen 21. Next the technician will place the cassette 12 with the film 15 and optical filter 30 in a plane parallel to the median plane 14 shown in FIG. 1 such that the axis 39 is substantially horizontal. Referring to FIG. 1, the cassette 12 can be further modified merely by simply marking lines 43 and 44 on the surface of the cassette to align with the boundaries 37 and 40.

Then the technician will select an exposure based upon the requirements for obtaining an image of the skeletal elements of the skull. As will now be apparent, in the areas of opacity the exposure of the film will be reduced by about 50% if the opaque portion 36 attenuates the energy from the reactant surface 25 fully. If the filter is constructed with an opaque portion 36 that is characterized by producing less than 100% attenuation, the exposure will increase accordingly.

Figure 5:
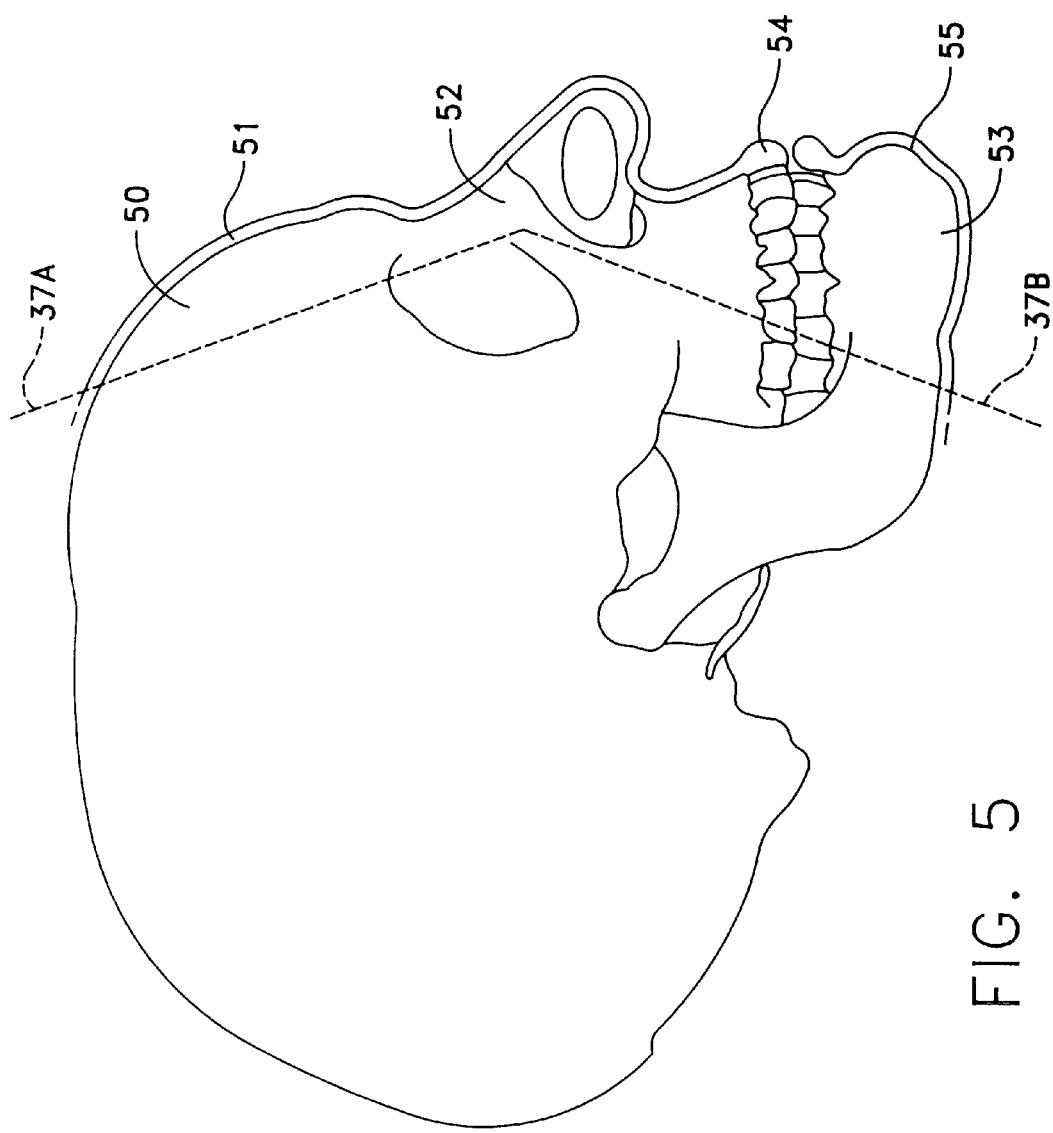
FIG. 5 represents an image produced on x-ray film in accordance with this invention.

FIG. 5 depicts the outline of an image that can be obtained with a cassette with uniformly responsive conversion screens acting on a double emulsion film. In this image the dashed lines 37A and 40A are placed as references to depict the position of the boundaries 37 and 40 in FIG. 4. In actual practice, if the band 41 is included in the filter, a smooth transition will occur between the images produced in alignment with the portions 36 and 31. If no such band 41 is included an actual line may be replicated in the image caused by the difference in exposures.

Still referring to FIG. 5, all the skeletal detail is not shown to the left of the lines 37A and 40A for clarity. Essentially the portion to the left of the lines 37A and 40A merely replicates a conventional cephalometric image as produced in the prior art. Unlike images obtained with prior art conventional cassettes, the image to the right of the lines 37A and 40A depicts the forehead portion of the skull 50 and the soft tissue 51 overlying the skull 50 in the forehead area. Likewise, the image depicts the soft tissue of the nose 52 and nasal passages. In the area of the lower jar 53, the image clearly depicts the lips 54 and the soft tissue around the chin 55. As will be apparent, that image of the soft tissue at 55 does not extend to the left of the line 40A because no filtering occurs to the left of the lines 37A and 40A.

As now will be apparent from FIG. 5, this invention provides a cephalometric image that depicts skeletal portions and, in areas aligned with the opaque portion of the filter, both skeletal and soft tissue images. This is particularly important. Many dental x-rays, as for use in orthodontal procedures, are enhanced if the interrelationship between the skeletal and soft tissue can be better understood and changes in the soft tissue anticipated if changes are made to the skeletal elements. Thus in accordance with the various objects of this invention, the film filter 30 provides a simple apparatus for providing such an enhancement of x-ray images of skeletal and soft tissue areas. This simple filter is particularly adapted for enhancing cephalometric x-ray images of skeletal portions of the skull and the soft tissue at the front of the head. The filter is easy to use as it is merely necessary to insert the filter against an existing screen in a standard cassette. As the filter is easily constructed, it is inexpensive to produce. Still further, the filter allows the easy conversion of a conventional x-ray film cassette for cephalometric imaging.

Moreover, it will become apparent that various modifications can be made to the specifically disclosed embodiment described above. The boundaries between the opaque and transparent portions can be shaped in any desirable configuration. The filter may omit the semi-opaque portion. For particular applications it may also be desirable to modify the degree of opacity in either the opaque, semi-opaque or both portions. Therefore it is an object of the claims to cover all such variations and modifications as come within the true spirit and scope of this invention.

What is claimed as new and desired to be secured by Letters Patent of the United States is:

1. Apparatus for enhancing a cephalometric image on a film produced by directing an x-ray beam from a source through a patient's head to a cassette containing the film in a plane parallel to the median plane, the cassette having first and second ends and a single uniformly responsive conversion screen means for responding to x-rays impinging on the screen means by producing energy that exposes the film, said apparatus including a sheet interposed between the film and the screen means, said sheet having an optically transparent portion and a substantially optically opaque portion, said optically opaque portion overlying the film proximate the front cassette and in an area that is in alignment with the patient's forehead and chin and said substantially transparent portion overlying substantially the remainder of the film whereby an image produced on the film depicts skeletal features in the area aligned with said transparent portion and skeletal and soft tissue features in the area aligned with the substantially optically opaque area.

2. Apparatus as recited in claim 1 wherein the width of the substantially optically opaque portion along the axis varies from a maximum at the edges of said sheet to a minimum substantially at the axis.

3. Apparatus as recited in claim 2 additionally including a portion of said sheet adjacent the substantially optically opaque portion that is semi-opaque.

4. Apparatus as recited in claim 3 additionally including means for removably fixing said sheet to the screen means.

5. A filter for enhancing a cephalometric image on a film produced by directing an x-ray beam from a source through a patient's head to a cassette containing the film that is pre-positioned to receive x-rays traversing the patient's head whereby the cassette extends along an axis, is parallel to the median plane and terminates in a forward end proximate the patient's forehead, nose and chin and a rearward end proximate the back of the patient's head, the cassette having first and second uniformly responsive conversion screens for responding to x-rays impinging on the screens by producing energy that exposes the film between the first and second screens, said filter including a sheet interposed between the film and one of the screens and having a substantially optically opaque portion extending perpendicularly to the axis and across said sheet to be aligned with the patient's forehead and chin and a substantially transparent portion extending across the sheet from the rearward end forward toward the opaque portion whereby an image produced on the film depicts skeletal features in the area aligned with said transparent portion and skeletal and soft tissue features in the area aligned with the substantially optically opaque area.

6. A filter as recited in claim 5 wherein the width of the substantially optically opaque portion along the axis varies from a maximum at the edges of said sheet to a minimum substantially at the axis.

7. A filter as recited in claim 6 additionally including a portion adjacent the substantially optically opaque portion that is semi-opaque.

8. A filter as recited in claim 7 additionally including means for removably fixing the filter to the screen.

9. A filter as recited in claim 7 wherein a plurality of spaced pads attached to the filter, each pad having an adhesive surface for affixing the filter to one of the screens.

10. A filter as recited in claim 5 wherein the x-rays from the patient pass through the first and second screens in order and said filter is disposed between the film and the second screen.

11. A filter as recited in claim 5 wherein the x-rays from the patient pass through the first and second screens in order and said filter is disposed between the film and the second screen.

12. A filter as recited in claim 10 wherein the width of the substantially optically opaque portion along the axis varies from a maximum at the edges of said sheet to a minimum substantially at the axis.

13. A filter as recited in claim 12 additionally including a portion adjacent the substantially optically opaque portion that is semi-opaque.

14. A filter as recited in claim 13 additionally including means for removably fixing the filter to said screen means.

15. A filter as recited in claim 13 wherein a plurality of spaced pads are attached to the filter, each pad having an adhesive surface for affixing the filter to one of the screens.

16. A cassette for use in obtaining a cephalometric image on an x-ray film comprising:

A) a frame elongated along a cassette axis for being disposed parallel to a median plane, B) first and second parallel conversion screens having a substantially uniform sensitivity to impinging x-rays across the area thereof, said cassette in use positioning the first conversion screen intermediate an x-ray source and the second conversion screen, C) means for holding a dual-emulsion film between said first and second conversion screens whereby energy from the first and second conversion means is directed toward film in said holding means, and D) a sheet filter formed of an exposed film sheet interposed between the film holding means and one of said conversion screens and having a substantially optically opaque portion extending across second exposed film sheet transversely to the cassette axis at one end of the cassette and extending axially to be in alignment with the forehead, nose and chin of a patient, said exposed film sheet additionally including a substantially transparent portion extending across said exposed film sheet and extending axially from the opaque portion to the other end of the cassette whereby an image produced on the dual-emulsion film depicts skeletal features in the area aligned with said transparent portion and skeletal and soft tissue features in the area aligned with the substantially optically opaque area.

17. A cassette as recited in claim 16 wherein the width of the substantially optically opaque portion along the axis varies from a maximum at the edges of said sheet filter to a minimum substantially at the axis.

18. A cassette as recited in claim 16 wherein said filter additionally includes a portion adjacent the substantially optically opaque portion that is semi-opaque.

19. A cassette as recited in claim 18 wherein the width of the substantially optically opaque portion along the axis varies from a maximum at the edges of said sheet filter to a minimum substantially at the axis and said semi-opaque portion has a fixed width.

20. A cassette as recited in claim 17 wherein said filter additionally includes means for removably fixing said sheet filter to said second screen means.

21. A cassette as recited in claim 16 wherein said sheet filter is positioned intermediate said film holding means and said second conversion screen.

22. A cassette as recited in claim 16 wherein said sheet filter is positioned intermediate said film holding means and said second conversion screen.

* * * * *